United States Patent [19]

Forester et al.

[11] Patent Number: 4,747,931
[45] Date of Patent: May 31, 1988

[54] COMPOSITION AND METHOD FOR COKE RETARDANT DURING PYROLYTIC HYDROCARBON PROCESSING

[75] Inventors: David R. Forester, The Woodlands; Dwight K. Reid, Houston, both of Tex.

[73] Assignee: Betz Laboratories, Inc., Trevose, Pa.

[21] Appl. No.: 47,740

[22] Filed: May 8, 1987

Related U.S. Application Data

[62] Division of Ser. No. 773,402, Sep. 6, 1985, Pat. No. 4,680,421.

[51] Int. Cl.$^4$ ................................................ C10L 1/10
[52] U.S. Cl. ...................... 208/14; 208/48 R; 208/48 AA; 585/950; 252/389.4; 252/8.3
[58] Field of Search ............... 208/48 R, 48 AA; 585/950; 252/389.4, 389.14

[56] References Cited

U.S. PATENT DOCUMENTS

| | | | |
|---|---|---|---|
| 2,914,481 | 11/1959 | Taylor, Jr. | 252/389.4 |
| 2,960,437 | 11/1960 | Meighen | 252/389.4 |
| 3,475,496 | 10/1969 | Sami et al. | 568/1 |
| 4,196,177 | 4/1980 | Sallay | 423/279 |
| 4,374,033 | 2/1983 | Malec | 252/49.6 |
| 4,382,025 | 5/1983 | Salley | 568/1 |
| 4,514,326 | 4/1985 | Sallay | 423/279 |
| 4,680,421 | 7/1987 | Forrester et al. | 208/48 AA |

FOREIGN PATENT DOCUMENTS 0125032 11/1984 European Pat. Off. ............... 568/1

*Primary Examiner*—Carl F. Dees
*Assistant Examiner*—Helane Myers
*Attorney, Agent, or Firm*—Alexander D. Ricci

[57] ABSTRACT

The present invention is directed to a method of inhibiting the formation of coke during the elevated temperature cracking of hydrocarbons. The method generally comprises adding to the hydrocarbon an effective amount of an ammonium borate, particularly ammonium biborate and ammonium pentaborate. Preferably, the ammonium borates are in a glycollic solvent or water.

6 Claims, No Drawings

COMPOSITION AND METHOD FOR COKE RETARDANT DURING PYROLYTIC HYDROCARBON PROCESSING

This is a division of application Ser. No. 773,402, filed on Sept. 6, 1985, now U.S. Pat. No. 4,680,421.

BACKGROUND OF THE INVENTION

The present invention is directed to a method and composition for use in inhibiting the formation and deposition of coke on surfaces during the elevated temperature processing of hydrocarbons. Coke deposition is generally experienced when hydrocarbon liquids and vapors contact the hot metal surfaces of the processing equipment. While perhaps not entirely technically understood, because of the complex makeup of the hydrocarbons, the hydrocarbons at elevated temperatures and in contact with hot metallic surfaces undergo various changes through either chemical reactions and/or decomposition of various unstable components of the hydrocarbon. The undesired products in many instances include coke, polymerized products, deposited impurities and the like. Whatever the undesired product that may be formed, the result is the smae, i.e., reduced economies of the process. If these deposits are allowed to remain unchecked, heat transfer, throughout and overall productivity are detrimentally effected. Moreover, downtime is likely to be encountered due to the necessity of either replacing and/or cleaning of the affected parts of the processing system.

While the formation and type of undesired products are dependent upon the hydrocarbon being processed and the conditions of the processing, it may generally be stated that such products can be produced at temperatures as low as 100° F.; but are much more prone to formation as the temperature of the processing system and the metal surfaces thereof in contact with the hydrocarbon increase. At these temperatures, coke formation is likely to be produced regardless of the type hydrocarbon being charged. The type coke formed, i.e., amorphous, filamentous or pyrolytic, may vary somewhat; however, the probability of the formation of such is quite high.

As indicated in U.S. Pat. Nos. 3,531,394 and 4,105,540 the teachings of which are incorporated herein by reference, coke formation and deposition are common problems in ethylene (olefin) plants which operate at temperatures where the metal surfaces in contact with the hydrocarbon are at 1600° F. and above. The problem is prevalent in the cracking furnace coils as well as in the transfer line exchangers where pyrolytic type coke formation and deposition is commonly encountered. Ethylene plants often referred to generally as "olefin plants", originally produced simple olefins such as ethylene, propylene, butanes and butadiene from a feed of ethane, propane, butanes and mixtures thereof. Later developments in the area of technology however, has led to the cracking of heavier feedstocks because of their availability to produce aromatics and pyrolsis gasoline as well as light olefins. Feedstocks now include light naphtha, heavy naphtha and gas oil.

According to the thermal cracking processes utilized in olefin plants, the feedstocks are cracked generally in the presence of steam in tubular pyrolysis furnaces. The feedstock is preheated, diluted with steam and the mixture heated in the pyrolysis furnace to about 1500° F. and above, most often in the range of 1500° to 1650° F. The effluent from the furnace is rapidly quenched by direct means or in exchangers which are used to generate high pressure steam at 400 to 800 psig for process use. This rapid quench reduces the loss of olefins by minimizing secondary ractions. The cooled gas then passes to the prefractionator where it is cooled by circulating oil streams to remove the fuel oil fraction. In some designs, the gas leaving the quench exchanger is further cooled with oil before entering the prefractionator. In either case, the heat picked up by the circulating oil streams is used to generate steam and to heat other process streams. The mixture of gas and steam leaving the prefractionator is further cooled in order to condense the steam and most of the gasoline product in order to provide reflux for the prefractionator. Either a direct water quench or heat exchangers are used for this cooling duty.

After cooling, cracked gas at, or close to atmospheric pressure, is compressed in a multistage compression system to much higher pressures. There are usually four or five stages of compression with interstage cooling and condensate separation between stages. Most plants have hydrocarbon condensate stripping facilities. Condensate from the interstage knockout drums is fed to a stripper where the $C_2$ hydrocarbons and lighter, are separated. The heavier hydrocarbons are fed to the depropanizer.

While various treatments have been proposed to eliminate or reduce filamentous coke formation at elevated temperatures, none have attained any great degree of success. In the book "Coke Formation on Metal Surfaces" by Albright and Baker, 1982, methods are described which utilize silicon and aluminum as pretreatments. In accordance with the procedure, the furnace tubes are pretreated with silicon and aluminum hours before introduction of the hydrocarbon feedstocks. With the use of silicon, furnace tubes are coated by the chemical vaporization of an alkoxysilane. While U.S. Pat. Nos. 4,105,540 and 4,116,812 are generally directed to fouling problems in general, the patents disclose the use of certain phsophate and phosphate and sulfur containing additives for use purportedly to reduce coke formation in addition to general foulants at high temperatue processing conditions.

With respect to coke retardation, various efforts have been reported, namely:

1. French Pat. No. 2,202,930 (Chem. Abstracts Vol. 83, 30687K) is directed to tubular furnace cracking of hydrocarbons where molten oxides or salts of group III, IV or VIII metals (e.g., molten lead containing a mixture of $K_3VO_4$, $SiO_2$ and NiO) are added to a pretested charge of, for example, naphtha/steam at 932° F. This treatment is stated as having reduced deposit and coke formation in the cracking section of the furnace.

2. Starshov et al, *Izv Vyssh. Ucheban. Zaved., Neft GAZ*, 1977 (Chem. Abst. Vol. 87: 154474r) describes the pyrolysis of hydrocarbons in the presence of aqueous solutions of boric acid. Carbon deposits were minimized by this process.

3. Nikonov et al., U.S.S.R. No. 834,107, 1981; (Chem. Abst. 95:135651v) describes the pyrolytic production of olefins with peroxides present in a reactor, the internal surfaces of which have been pretreated with an aqueous alcoholic solution of boric acid. Coke formation is not mentioned in this patent since the function of the boric acid is to coat the inner surface of the reactor and thus decrease the scavenging of peroxide radicals by the reactor surface.
4. Starshov et al., *Neftekhimiya* 1979 (Chem. Abst: 92:8645j) describes the effect of certain elements including boron on coke formation during the pyrolysis of hydrocarbons to produce olefins.
5. U.S. Pat. No. 2,063,596 discusses in its prior art section the problems associated with the processing of hydrocarbons in equipment whose metallic parts have been supplied with a metalloid. The general impression is that such has not been utilized successfully.
6. U.S. Pat. No. 1,847,095 in a somewhat ambiguous manner describes the use of metalloid compounds such as boron hydride which are capable of yielding "volatile hydrogen" during the processing of hydrocarbons. The patent is silient as regards the type of coke encountered and the problems associated therewith and contains no disclosure or suggestion relative to other boron compounds which may be utilized during the processing of hydrocarbons for protection against coke formation.
7. Baker, R. T. K., Gas Chem. Nucl. React. Large In dust. Plant, Proc. Conf., 1980. Chem. Ab. Vol. 94, 1981, 94:8141h, is directed to the role of various additives e.g., $B_2O_3$ in effecting the growth rate of filamentous coke produced from the decomposition of $C_2H_2$ on Ni-Fe or Mo Catalysts. $B_2O_3$ is stated as being the only additive which failed to provide any significant reduction in the growth of the filaments.

DESCRIPTION OF THE INVENTION

Generally the invention entails the use of certain boron compounds, and compositions containing such, to inhibit the formation and deposition of coke on metallic surfaces in contact with a hydrocarbon (either in liquid or gaseous form) which surfaces reach temeratures of 1400° F. (or 1450° F.) and above most often 1500°–2050° F.). These temperatures are commonly encountered as earlier indicated in the olefin plants. In these systems the components of the furnace (pyrolytic) as well as the ancillary parts are composed of ferrous metal. Iron, as well as iron alloys such as low and high carbon steel, and nickel-chromium-iron alloys are customarily used for the production of hydrocarbon processing equipment such as furnaces, transmission lines, reactors, heat exchangers, separation columns, fractionators, and the like.

The present inventor discovered that coking during the high temperatures cracking of hydrocarbons may be significantly reduced on the iron based and nickel-based surfaces of processing equipment by adding to the hydrocarbon feed stock or charge before and/or during cracking, ammonium borates and in particular ammonium pentaborates and biborates or compositions containing such.

The ammonium borates are effective when formulated with glycollic-type solvents, in particular ethylene glycol, propylene glycol and the like since they produce marketable and easily fed solutions. Aqueous solutions or simply water solutions of the ammonium borates are also effective.

The ammonium borate compounds may be dissolved in the water or the glycol carriers in any proportions, to produce a product which will provide the necessary amount of boron to any coke-formation prone environment to effectively eliminate or in the least minimize such. Coking is a significant problem and if left untreated will eventually shut the operation down. Accordingly it would be desirable to assure that any product used is either high in boron content or if not high in boron content is fed to the charge at high dosage rates to assure the availability of boron. Accordingly, product formulation lends itself to great flexibility.

Generally the product can contain on a weight basis from about 1 to 50% ammonium borate, with the remainder being the carrier, for example ethylene glycol. To assure maintenance of the solution during storage and exposure to different and perhaps drastic temperature conditions or to protect the solution during transportation, various stabilizing agents may also be added to the formulation as well as any preservative which might be desirable.

Typical formulations would be as follows:

| Ingredient | Percentage by Weight | |
|---|---|---|
| | Actual | Range |
| Ammonium borate compound | 10–15% | 1–50 |
| Solvent | 90–85% | 50–1 |

The treatment dosages again are dependent upon the severity of the coking problem, location of such, and of course, the amount of boron based compound in the formulated product. Perhaps the best method of describing the treatment dosage would be based upon the actual amount of "boron" that should be added to the charge. Accordingly the amount of formulated product to be added to a charge should be such to provide 0.1 ppm to 5,000 ppm, and preferably 0.5 ppm to 1000 ppm, of boron to said hydrocarbon charge. When ammonium biborate or pentaborate is added together with the carrier to the hydrocarbon feed stock in 0.1 to 5,000 ppm (B), the borates are present in the combination in an amount of 0.0001 to 2.5% by weight.

EXAMPLES

In order to establish the efficacy of the inventive concept various tests were conducted utilizing a propane feedstock with dilution steam added to enhance cracking. The apparatus and procedure used for the testing were as follows:

APPARATUS

The High Temperature Fouling Apparatus (HTFA) consists of five subsections which together simulate the pyrolysis of gaseous hydrocarbons to make light olefins and the coke formed on the heated metal surfaces during the pyrolysis reaction.

The feed preheat section is built of 316 stainless steel tubing and fittings and allows the mixing of nitrogen or oxygen containing gas with steam during the bring up and shut down of the HTFA and the propane and steam during the actual test. Steam is supplied at 40 psig by a steam generator and nitrogen, oxygen containing gas, or propane from compressed gas cylinders. The gases and steam are heated to about 400° F. at which point small amounts of water (blank test) or antifoulant is slowly injected into the stream by a syringe pump.

Following antifoulant injection, the gases flow through a coiled 316SS tube inside an electrically heated furnace. The gases are heated to 110°–1200° F. at the furnace exit at a furnace temperature of approximately 1865° F.

Following the furnace tube, the gases travel through the coker rod assembly. This consists of a 316SS rod which is electrically heated to 1500° F. while the gases flow around the heated rod inside a 316SS shell. The rod is electrically heated through a silicon controlled rectifier (SCR), then through two 4 to 1 stepdown transformers in series to achieve low voltage (3-4 volts), high amperage (200 amps) heating of the rod. A temperature controller is used to achieve power control through the SCR to obtain a 1500° F. rod temperature.

Upon exiting the coker rod, the gases pass through a condenser coil and then two knock-out flasks in ice baths to remove the water (steam) from the product gases. The remaining entrained water vapor in the gases is removed by passing through drierite.

The specific gravity of the product gas is determined in a gas densitometer and the gases analyzed using gas chromatography to determine yields. The remaining gases are vented through a safety hood exhaust.

TEST PROCEDURE

The furnace was turned on and the temperature thereof was stablized at 1200° F. with the coker rod reaching a temperature of 1500° F. while feeding nitrogen and steam. Oxygen feed containing gas and steam was then commenced and the furnace temperature permitted to increase to about 1450° F. (requiring approximately 10 min.).

Nitrogen feed which was stopped during the oxygen containing gas feed, was then again initiated, and the rod temperature permitted to decrease to 1200° F. Furnace temperatures were then slowly increased to 1800° F. over a period of 10 min. while the coke inhibitor or water (blank) as the case may be was injected into the mixed gas/steam line prior to the furnace at about 400° F. gas temperature.

The rod temperature was again increased to 1500° F., then nitrogen feed gradually switched to propane feed (about 2 min.). The temperature of furnace was then increased to about 1865° F. over approximately 30 minute period. The product gases were analyzed by gas chromatography and the temperatures, flowrates, pressures and product gas gravity recorded every 35 minutes during the 160 min. test on propane/steam feed. Gases exit the furnace tube at about 1150°-1250° F. and exit the coker shell at about 975°-1000° F. temperatures.

During a normal 160 minute run, approximately 3200-3300 grams of propane are fed and 1500-2000 grams of steam (determined from the condensate collected) for hydrocarbon to steam rates of about 1.6:1 to 2.2:1.

Following shutdown and cooling, the furnace tube and coker shell are cleaned and the coke collected and weighed.

The coke is burned to determine how much is non-coke (metal corrosion products). After a series of blanks (water) and antifoulant tests are conducted, a steam to coke relationship is determined for the blanks of A/x(condensate rate) and the predicted cokes compared to actual cokes of the treatments to determine percent coke reduction.

RESULTS

The data collected from the experiments using propane/steam feed and injecting water during blanks (controls) or ammonium borate feeds are set forth below in Table 1.

TABLE 1

| | | HTFA Data-Decoked Procedure-Propane Feed Boron Containing Coke Retardants | | | | | | | |
|---|---|---|---|---|---|---|---|---|---|
| Additive | Solvent | Furnace Tube | Run No. | Cond. Rate, Ml/Min | Coke Gms. | PPM B | Non-Coke Gms. | 1 Pred Coke | 2 % Prot |
| Blank | H₂O | 16 | 5 | 6.70 | .94 | 0 | .07 | .91 | −3 |
| Blank | H₂O | 15 | 2 | 8.00 | .71 | 0 | .09 | .77 | 7 |
| Blank | H₂O | 16 | 6 | 6.00 | 1.15 | 0 | .32 | 1.02 | −13 |
| Blank | H₂O | 17 | 2 | 6.40 | 2.19 | 0 | .05 | .96 | −129 |
| Blank | H₂O | 17 | 7 | 6.45 | 1.97 | 0 | .06 | .95 | −107 |
| Blank | H₂O | 17 | 10 | 7.51 | 1.07 | 0 | .11 | .81 | −31 |
| Blank | H₂O | 18 | 2 | 7.07 | .32 | 0 | .06 | .87 | 63 |
| Blank | H₂O | 18 | 12 | 7.46 | .66 | 0 | .05 | .82 | 20 |
| Blank | H₂O | 18 | 15 | 8.66 | 1.37 | 0 | .13 | .71 | −94 |
| Blank | H₂O | 18 | 20 | 7.01 | .55 | 0 | .06 | .87 | 37 |
| Blank | H₂O | 18 | 25 | 5.18 | .43 | 0 | .08 | 1.18 | 63 |
| Blank | H₂O | 19 | 2 | 6.55 | .74 | 0 | .20 | .93 | 21 |
| Blank | H₂O | 19 | 8 | 6.43 | .55 | 0 | .12 | .95 | 42 |
| Blank | H₂O | 19 | 13 | 8.64 | 1.14 | 0 | .24 | .71 | −61 |
| Blank | H₂O | 19 | 19 | 9.22 | .14 | 0 | .07 | .66 | 79 |
| Blank | H₂O | 19 | 20 | 7.88 | .38 | 0 | .11 | .78 | 51 |
| Blank | H₂O | 19 | 27 | 4.13 | 2.74 | 0 | .28 | 1.48 | −85 |
| Blank | H₂O | 20 | 2 | 10.09 | .73 | 0 | .08 | .61 | −20 |
| Blank | H₂O | 20 | 8 | 7.95 | .77 | 0 | .04 | .77 | 0 |
| Blank | H₂O | 20 | 14 | 10.55 | .71 | 0 | .23 | .58 | −22 |
| Blank | H₂O | 20 | 20 | 8.72 | .21 | 0 | .26 | .70 | 70 |
| Blank | H₂O | 21 | 2 | 6.95 | .20 | 0 | .05 | .88 | 77 |
| Blank | H₂O | 21 | 3 | 5.82 | .49 | 0 | .06 | 1.05 | 53 |
| Blank | H₂O | 21 | 7 | 8.64 | .52 | 0 | .04 | .71 | 27 |
| Blank | H₂O | 21 | 13 | 7.33 | .77 | 0 | .11 | .83 | 8 |
| Blank | H₂O | 21 | 20 | 8.48 | .44 | 0 | .12 | .72 | 39 |
| Blank | H₂O | 22 | 8 | 7.39 | .74 | 0 | .23 | .83 | 11 |
| Blank | H₂O | 22 | 14 | 7.64 | .74 | 0 | .31 | .80 | 8 |
| Blank | H₂O | 22 | 20 | 8.72 | .37 | 0 | .48 | .70 | 47 |
| (NH₄)2B10O16 | 14.5%/EG | 17 | 5 | 7.70 | .78 | 71 | .05 | .79 | 2 |
| (NH₄)2B10O16 | 15%/EG | 18 | 8 | 7.40 | .98 | 45 | .09 | .83 | −18 |
| (NH₄)2B10O16 | 15%/EG | 18 | 13 | 7.59 | .24 | 44 | .05 | .81 | 70 |
| (NH₄)2B10O16 | 15%/EG | 18 | 21 | 8.48 | .17 | 44 | .06 | .72 | 76 |
| (NH₄)2B10O16 | 10%/H₂O | 21 | 18 | 9.59 | .31 | 27 | .06 | .64 | 51 |
| (NH₄)2B10O16 | 10%/H₂O | 22 | 13 | 8.48 | .28 | 27 | .11 | .72 | 61a |

TABLE 1-continued

HTFA Data-Decoked Procedure-Propane Feed
Boron Containing Coke Retardants

| Additive | Solvent | Furnace Tube | Run No. | Cond. Rate, Ml/Min | Coke Gms. | PPM B | Non-Coke Gms. | 1 Pred Coke | 2 % Prot |
|---|---|---|---|---|---|---|---|---|---|
| (NH₄)2B4O7 | 15%/EG | 18 | 9 | 8.24 | .63 | 38 | .05 | .74 | 15 |
| (NH₄)2B4O7 | 15%/EG | 18 | 24 | 9.42 | .15 | 37 | .04 | .65 | 77 |
| (NH₄)2B4O7 | 15%/EG | 19 | 14 | 9.65 | .41 | 36 | .10 | .63 | 35 |
| (NH₄)2B4O7 | 10%/EG | 19 | 22 | 8.83 | .18 | 24 | .12 | .69 | 74 |
| (NH₄)2B4O7 | 10%/EG | 20 | 4 | 10.25 | .46 | 22 | 1.33 | .60 | 23 |
| (NH₄)2B4O7 | 10%/EG | 20 | 6 | 9.62 | .29 | 24 | .22 | .64 | 54 |
| (NH₄)2B4O7 | 10%/EG | 21 | 19 | 8.38 | .52 | 25 | .22 | .73 | 29 |
| (NH₄)2B4O7 | 10%/H₂O | 20 | 5 | 8.36 | .39 | 24 | .18 | .73 | 47 |
| (NH₄)2B4O7 | 10%/H₂O | 20 | 7 | 8.04 | .39 | 23 | .07 | .76 | 49 |
| (NH₄)2B4O7 | 10%/H₂O | 21 | 4 | 9.56 | .82 | 22 | .19 | .64 | −28 |
| (NH₄)2B4O7 | 10%/H₂O | 21 | 21 | 8.58 | .29 | 22 | .06 | .71 | 59 |
| (NH₄)2B4O7 | 10% in H₂O/EG(3) | 20 | 9 | 7.54 | .40 | 22 | .06 | .81 | 51 |
| (NH₄)2B4O7 | 10% in H₂O/EG(3) | 22 | 15 | 8.15 | .76 | 23 | .46 | .75 | −1 |

1 Predicted coke = 6.12/condensate rate (ml/min)
2 (1-coke/predicted coke) × 100%
EG Ethylene Glycol
a Partially plugged coke inhibitor feed line
(3) Ratio of H₂O/EG is 3:1

A summary of the tests conducted, and results obtained are set forth in Table 2 below. Two different but well known statistical procedures were utilized in analyzing the data.

A-B represents the Ansari-Bradley statistical procedure and M-W represents the Mann-Whitney procedure, each of which utilizes its particular manner of developing its particular expression of confidence level.

TABLE 2

Summary of HTFA Results on Boron Antifoulants

| Additive | # of Runs | Coke Protection % | | | | Statistical Analysis | |
|---|---|---|---|---|---|---|---|
| | | Range | Avg. | SD | Median | A-B (SL)* | M-W (#/CV)** |
| Blank/H₂O | 29 | −129/79 | 5.2 | 56 | 11 | — | — |
| (NH₄)2B10O16 | 6 | −18/76 | 40 | 39 | 56 | .239 | 120.5/126 |
| (NH₄)2B4O7 | 13 | −28/77 | 37 | 30 | 47 | .047 | 254/250 |

*Significance level (0.05 is 95% confidence level additive protection is greater than blank protection).
**Calculated number vs. critical value for 95% confidence additive protection greater than blank protection.

From the data summarized in Table 2, it can be seen that both ammonium borates tested provided averages of 32–35% reduction in coke formation vs. control tests. In addition, ammonium biborate provided protection significantly greater than the control experiments at 95+% confidence level. The significance confidence limit for the ammonium pentaborate protection levels was below 95% due in part to fewer experimental runs than with ammonium biborate.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

We claim:

1. A hydrocarbon which is to be subjected to thermal cracking to whch hydrocarbon has been added a composition comprising an ammonium borate contained in a water, glycolic or water-glycolic carrier.

2. A hydrocarbon according to claim 1 wherein the borate is selected for the group consisting of ammonium biborate and ammonium pentaborate.

3. A hydrocarbon according to claim 2 wherein said glycollic carrier is selected from the group of ethylene glycol and propylene glycol.

4. A hydrocarbon according to claim 3 which contains on a percentage by weight basis 0.0001 to 2.5% of said borate.

5. A hydrocarbon according to claim 4, 3 or 1 wherein said borate is ammonium biborate and such is in the composition in about 0.0001 to 2.5% by weight.

6. A hydrocarbon according to claims 4, 3 or 1 wherein the borate is ammonium pentaborate and such is in the composition in about 0.0001 to 2.5% by weight.

* * * * *

UNITED STATES PATENT AND TRADEMARK OFFICE
CERTIFICATE OF CORRECTION

PATENT NO. : 4,747,931
DATED : May 31, 1988
INVENTOR(S) : Forester et al

It is certified that error appears in the above-identified patent and that said Letters Patent is hereby corrected as shown below:

Col. 2, line 5, change "ractions" to --- reactions ---.
Col. 3, line 17, change "silient" to --- silent ---.
Col. 3, line 38, change "temera-" to --- tempera- ---.
Col. 3, line 50, change "inventor" to --- inventors ---.
Col. 3, line 51, change "temperatures" to --- temperature ---.
Col. 3, line 59, change "glycollic" to --- glycolic ---.
Col. 4, line 66, change "110°" to --- 1100° ---.
Col. 5, line 25, change "feed containing gas" to --- containing gas feed ---.
Table 1&2, change every occurrence of "(NH4)2B10O16" to --- $(NH_4)_2B_{10}O_{16}$ ---.

Table 1&2, change every occurrence of "(NH4)2B4O7" to --- $(NH_4)_2B_4O_7$ ---.

col. 8, line 46, change "glycollic" to --- glycolic ---.

Signed and Sealed this

Twenty-second Day of November, 1988

Attest:

DONALD J. QUIGG

*Attesting Officer*    Commissioner of Patents and Trademarks